United States Patent [19]

Lundin et al.

[11] 4,246,340
[45] Jan. 20, 1981

[54] METHOD AND REAGENT FOR BIOLUMINISCENCE

[75] Inventors: Arne T. Lundin, Stockholm; Arne Myhrman, Solna, both of Sweden

[73] Assignee: LKB-Producter AB, Bromma, Sweden

[21] Appl. No.: 43,835

[22] Filed: May 30, 1979

[30] Foreign Application Priority Data

May 31, 1979 [SE] Sweden .............................. 7806296

[51] Int. Cl.³ ............................................. C12Q 1/66
[52] U.S. Cl. ......................................... 435/8; 435/184
[58] Field of Search ..................... 435/4, 8, 184, 810; 424/2

[56] References Cited

U.S. PATENT DOCUMENTS

| | | | |
|---|---|---|---|
| 3,575,811 | 4/1971 | Chappelle | 435/8 |
| 3,575,812 | 4/1971 | Chappelle | 435/8 |
| 3,616,253 | 10/1971 | D'Eustachio | 435/8 |
| 3,929,586 | 12/1975 | Forgione | 435/17 |
| 3,933,592 | 1/1976 | Clendenning | 435/17 |
| 4,001,088 | 1/1977 | Antonik | 435/8 |
| 4,080,265 | 3/1978 | Antonik | 435/8 |

FOREIGN PATENT DOCUMENTS 2001434 1/1979 United Kingdom ..................... 435/8

OTHER PUBLICATIONS

"Immobilized Firefly Luciferase," Lee, Analytical Biochemistry 80 (1977) pp. 496-501.

Primary Examiner—Ernest G. Therkorn
Attorney, Agent, or Firm—Fisher, Christen & Sabol

[57] ABSTRACT

An improvement in the process for the determination of the concentration of adenosinetriphosphate (ATP) in ATP-converting reactions wherein the concentration is a function of the intensity of light emitted when a sample to be assayed is contacted with a bioluminescent reagent based on D-luciferin, luciferase and magnesium ions or certain other metal ions, the emitted light resulting from ATP and D-luciferin becoming bound to the luciferase, comprises the use of one or more competitive inhibitors such as a D-luciferin analogue, or analogues.

16 Claims, 2 Drawing Figures

REACTIONS CATALYSED BY FIREFLY LUCIFERASE

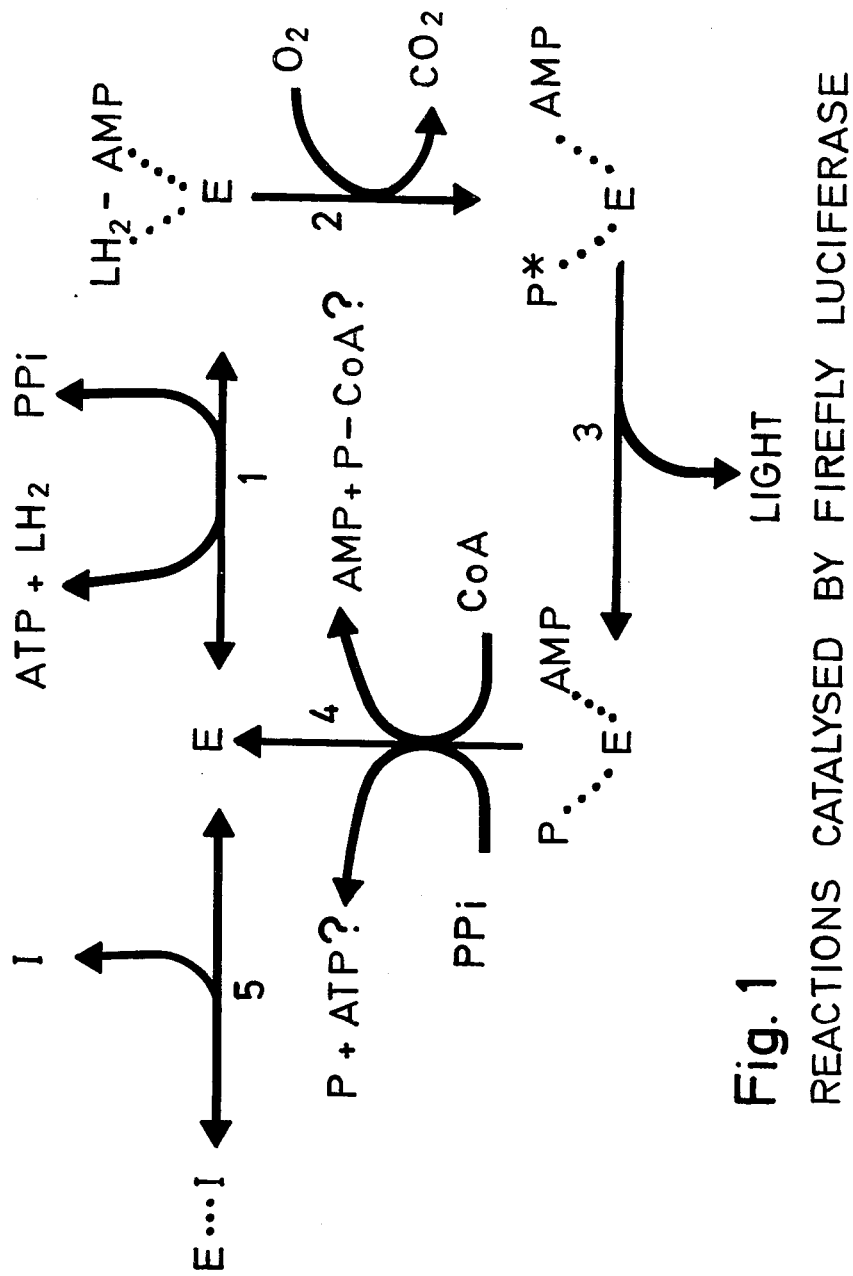
Fig. 1 REACTIONS CATALYSED BY FIREFLY LUCIFERASE

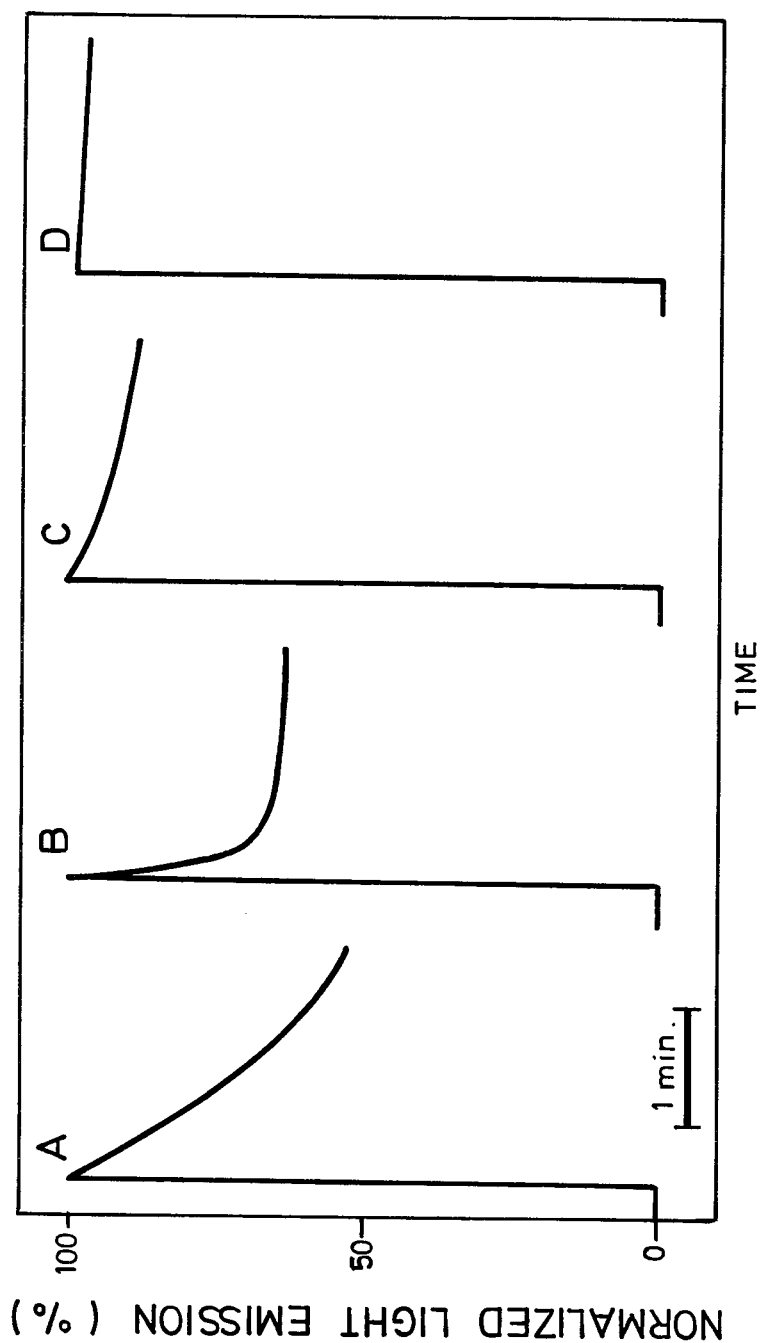
Fig. 2 TIME COURSE OF LIGHT EMISSION IN THE PRESENCE OF VARIOUS ADDITIVES.

METHOD AND REAGENT FOR BIOLUMINISCENCE

The present invention refers to a method and a reagent to be used in determining the ATP-concentration in e.g. ATP-converting systems. More particulay the invention refers to a technique in which said system is brought into contact with a bioluminiscence reagent based o D-luciferin, luciferase and magnesium ions or certain other metal ions whereby a reaction takes place in which ATP and D-luciferin are bound to be luciferase and light is emitted and where the intensity of the emitted light is measured, said intensity being a measure of the ATP concentration.

According to the invention additives to an ATP dependent bioluminiscence reagent result in a light emission which during the complete measuring time has the same proportionality factor to the ATP concentration. As the bioluminiscence reagent itself consumes negligible amounts of ATP, samples with a constant ATP concentration will give rise to a constant light emission which facilitates the use of the reagent for ATP determination. Furthermore, a reagent with the above cited properties can be added to other ATP converting systems so as to in a simple manner make it possible to monitor changes in the ATP concentration by means of a continuous measurement of the light intensity. ATP converting systems could e.g. be combinations of enzymes and possible a substrate which at a reaction give rise to a binding or consumption of ATP. The analytical use of the reagent comprises determining of ATP and substances and enzymes taking part in ATP converting reactions within clinical chemistry and clinical microbiology and within biochemical and biological research (especially bioenergetics).

ATP dependent bioluminicense reagents, where ATP is the commonly used abbreviation for adenosinetriphosphate, are known per se, said reagents being based on an enzyme, luciferase, and one of the two substrates, namely D-luciferin and magnesium ions and certain other metal ions to which the other substrate, ATP, has to be complex bound in order to react. When ATP is brought in contact with the reagent, the reaction or rather the sequence of luciferase catalyzed reactons which in a schematically simplified and partly hypothetical form are shown in FIG. 1 will take place. The reactions 1–3 have been studied in detail for luciferase from the common American firefly *Photinus pyralis* and these reactions represent the prior art. Several survey articles have been published in recent years, see DeLuca, M. (1976), "Advance in Enzymology"., (A. Meister. ed.) Vol. 44, 37–68, John Wiley & Sons, New York and McElroy, W. D., Seliger, H. H. and DeLuca, M. (1974), "The Physiology of Insecta", 2nd ed (M. Rockstein, ed.) Vol. 11, 411–460, Academic Press, New York.

In reaction 1 there is formed from luciferase (E), ATP and D-luciferin ($LH_2$), free pyrophosphate (PPi) and enzyme bound luciferyladenylate. This reaction is not limiting for the rate of the complete reaction. The enzyme-luciferyladenylate complex obtained is subect to two processes limiting the speed of the initially emitted light, namely a conformation change and an abstraction of a proton from luciferyladenylate (see DeLuca, M. and Mc Elroy, W. D., (1974), Biochemistry, 13, 921–925). In reaction number 2 luciferyladenylate is oxidized with oxygen under production of AMP (adenosinel monophosphate) and excited oxyluciferin ($P^x$), which both remain enzyme bound, and carbon dioxide. Oxyluciferin is in reaction 3 transformed into its ground state while emitting a photon. The energy for emitting the photon has been obtained from the oxidation of luciferin and not from splitting of the pyrophosphate bound in ATP.

The enzyme-oxyluciferin-AMP-complex generated in reaction 3 is stable and can be isolated by gel filtration if the reaction is performed in the presence of pyrophosphatase (Gates, B. J., and DeLuca, M. (1975) Arch., Biochem, Biophys., 169, 616–621). In the absence of pyrophosphatase an enzyme-oxyluciferin-complex is isolated without AMP, having the same activity as a free enzyme (see the last mentioned article of Gates and DeLuca).

The stability of the enzyme-oxyluciferin-AMP-complex results in that the mixture of luciferase, D-luciferin and ATP give rise to a light flash rather than a constant light emission. The maximum light intensity will be reached within one second and is thereafter declining to a steady-state level, where the regeneration of free enzyme is obtained with essentially the same speed as the light emission. The steady-state level is, however, not completely constant mainly because of the fact that the free products are inhibiting the reactions.

The determination of ATP has usually been made in such a way that the sample with an unknown ATP-concentration has been mixed with the bioluminiscent reagent which contains luciferase, D-luciferin and magnesium ions. In order to obtain a maximum reliability of the analysis the mixing should suitably take place with a given reaction rate and in a measuring position so that the initial parts of the light characteristics can be registered (see Lundin, A. and Thore, A. (1975) Anal. Biochem., 66, 47–63). When the measure of the light intensity used for the determination has been registered, the analysis is repeated with a sample containing a known ATP-concentration and with a blank without ATP. From these three measurements the unknown ATP-concentration has been calculated. If the sample has contained substances which could interfere with the analysis an internal standard technique has been used, i.e. the sample has been analysed with and without addition of a known ATP concentration.

Already in 1952 it was shown that ATP dependent bioluminiscence systems are available not only for determining the ATP, but also in principle for determining any substance which takes part in ATP converting reactions (Strehler, B. L. and Totter, J. R. (1952) Arch. Biochem. Biophys. 40, 28–41). The possibility of adding a bioluminiscent reagent to an ATP converting system in order to continuously follow the ATP concentration by measuring the light intensity has, however, obtained very little practical significance. This is due partly to the fact that the activity of the luciferase during the reaction declined by means of product inhibition as described above, partly because of the fact that the luciferase reagents have been contaminated with ATP converting systems. The interest of the method has, however, raised when it has become possible, by means of using purified luciferase and with a synthetical preparation of the luciferin, to obtain during a reaction time of several minutes a negligible decrease of the light intensity as well as of the ATP concentration (Lundin, A. and Thore A. (1975) Anal. Biochem. 66, 47–63. Suitable conditions for the analysis have been investigated and the method has proven useable for ATP concentrations up to $10^{-6}$ M (Lundin, A., Rickardsson, A. and Thore, A., (1977), Anal. Biochem. 75, 611–620). In spite of repeated experiments a reagent with the above cited properties could be prepared only in very few cases.

It has however been possible to show the analytical use of a reagent with the above cited properties for kinetic determinations of subtrates and enzymes, for end-point determination of substrate, to monitor photo-phosphorylation and to follow lytic reactions (Lundin, A., Rickardsson, A., and Thore, A. (1976), Anal. Biochem. 75, 611–620; Lundin A., Rickardsson, A., and Thore, A. (1977), "Proceedings of the 2nd Bi-Annual ATP Methodology Symposium," SAI Technology Company, San Diego; Lundin, A., Thore, A. and Baltscheffsky, M. (1977), FEBS Lett. 79, 73–76; Lundin, A. (1978), "Methods in Enzymology" (M. DeLuca, ed.) Vol. 57, Academic Press, New York; Lundin, A. and Baltscheffsky, M. (1978) "Methods in Enzymology"0 (M. DeLuca, ed.) Vol. 57, Academic Press, New York; Lundin A., and Styrelius, I., (1978) Clin. Chem. Acta and Thore A., and Eriksson, A. C. (1977), FOA-report.

The difficulties in preparing in a reproducible way a reagent with the above cited properties have, however, implied that the above cited applications have not obtained any use outside the laboratory at which the technique was developed.

Before the use of the present invention the stability of the light level varied in different reagents from a decline of a few percent per minute to a decline to half the initial light intensity after one minute. According to the present invention it has, however, been shown that an addition of D-luciferin analogs make it possible to prepare in a reproducible way a reagent with the desired properties, i.e. with a stable light level. The effect of the D-luciferin analogs of the stability of the light level has not previously been observed and it should in analytical applications be closely at hand to avoid said analogs as they have been shown to inhibit the light reaction competitively with the D-luciferin (Denburg, J. L.)

With a D-luciferin analog is meant in connection with this invention substances which inhibit the previously described luciferase reaction and this inhibition being competitive with respect to D-luciferin. The specific D-luciferin analogs giving the desired result are easily found by adding them in inhibiting concentrations to the reagent and measuring the stability of the light level after addition of ATP.

Although the invention is not limited to any specific theory as concerns the reaction mechanics at the addition of a D-luciferin analog, said addition could mean that a smaller part of the total luciferase amount will exist as an inactive enzyme-product-complex.

As the free enzyme concentration decreases by forming of an enzyme-product complex, the enzyme-luciferin analog complex is probably dissociated under formation of free enzyme as is shown in the reaction 5 in FIG. 1 where I represents the D-luciferinanalog. By using the D-luciferin-analog, i.e. the competitive inhibitor, the luciferase amount can be increased without any corresponding increase of the reaction rate. This is true irrespectively of whether the D-luciferin analog reacts with ATP according to reaction 1 or is forming an enzyme inhibiting complex according to reaction 5. The essential prerequisite is solely that the reactions are reversible and are faster than reactions 2–4 (reaction 4 will be discussed in detail below).

To the extent free AMP and free oxluciferin are formed in the reaction it could also be of interest to study whether this would affect the product inhibition. If e.g. $10^{-6}$ M ATP would lead to a generation of $10^{-6}$ M AMP and $10^{-6}$ M oxyluciferin the inhibition of AMP would, as $K_i$ for AMP is $2.4\times 10^{-4}$ M (see Lee, R. T., Denburg, J. L. and McElroy, W. D. (1970) Arch. Biochem. Biohpys, 141, 38–52) affect the luciferase activity by less than 0.5%. On the other hand the forming of oxyluciferin, the $K_i$ value on which is $2.3\times 10^{-7}$ M (Goto, T., Kubota, I., Suzuki, N. and Kishi, Y. (1973) "Chemiluminiscence and Bioluminiscence" (M. J. Cormier, D. M. Hercules, and J. Lee, eds.) pages 325–335, Plenum Press, New York) would decrease the luciferase activity significantly. Consequently it may under certain conditions be important to counteract the effect of the generation of free oxyluciferin. The addition of D-luciferin analog makes the initial inhibition of the luciferase so big that the additional inhibition from the oxyluciferin, which is continuously formed during the reaction, will be negligible. The addition of inhibiting concentrations of a D-luciferin analog will thus stabilize the light level.

In the analysis the concentration of D-luciferin should be saturating i.e. so high that a small change of the concentration will not affect the reaction rate. This is essential as small changes in volume would otherwise affect the reaction rate. Furthermore, components of biological samples could affect the D-luciferin concentration available for the luciferase reaction and thus inhibit that reaction. A satisfactory accuracy of the analysis could thus only be achieved by using saturating concentrations of D-luciferin.

By adding a D-luciferin-analog to D-luciferin and apparent saturation can be achieved at a low concentration of D-luciferin without affecting the accuracy of the analysis in any other way than by a reducing of the sensitivity. This is an additional advantage of the invention, since D-luciferin is an expensive substance which only in exceptional cases can be added in saturating concentrations.

The reduced luciferase activity obtained by the addition of an analog can be compensated by an increase of the luciferase concentration. Thus, the luciferin-luciferase ratio can be optimized with respect to e.g. cost for reagent production without affecting the sensitivity of the analysis. The importance of the invention in this respect is easily realized from the fact that the world market for only one of the developed applications is about 5 millions analyses per year. Thus a decrease of the cost for the reagent by less than one cent per analysis will imply considerable reductions in cost which means that the present invention also in this respect involves a very essential contribution to the technique in the field.

In summary, it could thus be concluded that the use according to the invention of the luciferin-analog makes it possible to optimize the luciferin/luciferase ratio with respect to e.g production cost of the reagent and also for increasing the stability of the light-level. A suitable concentration of the D-luciferin analog is one which gives an inhibition of the luciferase reaction, and thus the light intensity, by at least 25% since at a lower degree of inhibition, the effect on the stability of the light level and the required concentration of the D-luciferin for saturation will be too small to be of economical analytical importance. A specifically preferred range is 50–90%. An inhibition of the intensity of more than 90% makes among other things the demands on the registration equipment unnecessary big and also makes it necessary to increase the amount of the luciferase so much that the analysis will be uneconomical. Furthermore, an analytical interference can easily be obtained at high amounts of luciferase.

In accordance with a specifically preferred embodiment of the invention the previously mentioned competitive inhibitor is added to the reagent together with pyrophosphate. It is known per se that concentrations of pyrophosphate which are inhibiting luciferase reaction, counteract the decline of the light intensity (McElroy, W. D., Hastings, J. W., Coulombre, J. and Sonnenfeld, V. (1953), Arch. Biochem. Biophys. 46 399–416). This has, however, never previously been used to improve the assay conditions in the determination of ATP.

According to the present invention it has surprisingly appeared that a combined use of pyrophosphate in a much lower concentration than it have been used before, preferably in a highest concentration $10^{-4}$ M and specifically not more than $10^{-5}$ M and a competitive inhibitor in the concentration defined above a very stable light level can be obtained. Through this combination the same stability of the light level can be achieved as would require a considerably higher degree of inhibition of the luciferase to achieve by use of either pyrophosphate of D-luciferin analog. At a competitive inhibition with a D-luciferin analog of around 50% and a concentration of pyrophosphate of $10^{-6}$ M it has thus been possible to achieve a decline of the light intensity curve which is below 3 percent and at an inhibition of around 75% and a concentration of pyrophosphate of $10^{-6}$ M it has been possible to achieve decline of the light intensity curve in the order of 1%. Such a stable light intensity will of course imply that much less expensive and simpler registration equipment can be used and above all it gives very good prerequisite for continuous analysis of ATP converting reactions.

Although the reaction in this respect is not limited in any specific theory concerning the reaction mechanics it is possible the pyrophosphate reacts with AMP in the enzyme-oxyluciferin-AMP complex according to reaction 4 of FIG. 1. The formation of ATP from pyrophosphate and AMP requires energy. This energy is probably obtained from the transformation of enzyme back to its original conformation from the conformation which was obtained before the oxidation reaction (reaction 2 of FIG. 1). The conformation change would explain why the product inhibition is non-competitive (Lemasters, J. J. and Hacknebrock, C. R. (1977) Biochemistry 16, 445–447) whereas oxylucuiferin is a competitive inhibitor (see the above cited application by Goto et al., 1973). The reaction with pyrophosphate would thus change a strong non-competitive inhibition (see the above cited publication by Goto et al., 1973) to a weaker competitive inhibition. The effect of the competitive inhibition on the light level could according to the invention be counteracted by means of adding a D-luciferin-analog (see above). According to reaction 4 of FIG. 1 the luciferase reaction in the presence of pyrophosphate does not give any net consumption of ATP. This would contribute to the stabilisation of the light level.

In addition to taking part in splitting enzyme from the enzyme-oxyluciferin-AMP-complex the pyrophosphate could in inhibiting concentrations contribute by driving the reaction 1 of FIG. 1 backwards. By adding pyrophosphate the total enzyme concentration could thus be increased without a corresponding increase of the light intensity. A smaller part of the total enzyme concentration will thereby be present as an inactive enzyme product complex. Inhibiting pyrophosphate concentrations would thus contribute to the stabilisation of the light level.

According to another preferred embodiment of the invention one could to the bioluminiscent reagent add co-enzyme A, i.e. either in combination with the competitive inhibitor only or in combination with the competitive inhibitor and pyrophosphate. Also, the addition of co-enzyme A has been shown to stabilize the light level. The fact that one could obtain an increase of the light intensity by adding only co-enzyme A is known per se e.g. by the publication of Airth, R. L., Rhodes, W. C. and McElroy, W. D. (1958), Biochem. Biophys, Acta, 27, 519-, but the use of co-enzyme A for improving the analysis conditions when determining ATP has not previously been suggested.

The reaction mechanics for co-enzyme A is thus probably that the compound reacts with oxyluciferin in the enzyme-oxyluciferin AMP-complex according to reaction 4 in FIG. 1 (where co-enzyme A is denoted CoA). The reaction between co-enzyme A and oxyluciferin changes the non-competitive product inhibition of the enzyme and oxyluciferin -AMP-complex to a weak competitive inhibition by AMP, which is negligible under normal analytical conditions.

Thus, coenzyme A will perform its effect without inhibiting the luciferase reaction. This is in contrast to D-luciferin analogs and in certain cases also to pyrophosphate. The inhibition obtained with D-luciferin analogs and pyrophosphate will however in many analytical applications not be of importance since the sensitivity of luciferase method generally will be satisfactory even after the inhibition. If this is not the case the concentration of the luciferase may be increased provided that the luciferase preparation does not contain to high proportions of contaminants interfering with the analysis. In certain applications of the present invention it could therefore be of special interest to use a hgihly purified luciferase preparation. Different methods for purifying luciferase are known per se and anyone of these methods could be used in most cases. A preferred embodiment of the invention, when the demands of purification are very high, woould be the use of a reagent which contains luciferase purified by means of isoelectric focusing. Luciferase could furthermore be protected from unspecific activation by means of chosing the correct reaction conditions and through addition of protecting substances such as e.g. bovine serumalbumin, thiol compounds and/or EDTA (Etylenediamin tetraacetic acid).

The use of pyrophosphate and coenzyme A may be limited by the existence in certain biological samples of enzyme systems which degrade these substances. In this cases the effect of such enzymes could be prevented by adding an inhibitor which does not affect the luciferase reaction. The pyrophosphatase activity could e.g be inhibited by mangan or fluoride ions. Considering the synthetic nature of the luciferin analogs these would presumably not be subject to an enzymatic degradation in biological samples.

When producing a bioluminiscence reagent with the desired properties the choice of substances or the combination of substances within the group of D-luciferin analogs, pyrophosphate and coenzyme A has to be determined by the application. This is due to the fact that the demands of different applications vary with respect to sensitivity, sample composition, existing interfering reactions, the price level of the reagent, storing stability etc. Considering that the present invention has made it possible to make the choice within a big group of substances it would, for the man skilled in the art, not imply any difficulties to find a suitable reagent composition for each single application.

In addition to the above mentioned advantages and the application of the present invention it may be added that continuous measurement of ATP converting reactions with the improved bioluminiscence reagent according to the invention has a sensitivity which normally is several powers of ten higher than the corresponding spectrophotometric method. The analytical procedure is however very similar to the procedure for coupled spectrophotometrical analysis based on e.g. NAD+/NADH-conversion. Also when determining ATP in non-ATP-converting systems, i.e. in samples with a constant ATP concentration, a reagent with the above cited properties has obvious advantages. Since the light is constant no demands are put on the velocity of mixing reagent and samples. The mixing does not have to take place in the measuring position and the light measurement may continue during any desired period of time. Thereby the sensitivity as well as the reproducibility will be increased. Also when determining ATP in cellular systems the reagent according to the invention has big advantages since it makes it possible to measure the concentration of extra cellular and intracellular ATP in the same sample. The concentration of extra cellular ATP is first measured whereafter some lytic reagent, which does not affect the luciferase system, is added and the light increase corresponding to the concentration of intracellular ATP is measured.

Although the single components of the bioluminiscent reagent according to the invention for simplicity's sake have been described as part of the reagent, it is of course possible to add them separately. Thus, one or several of the components can be added together with the buffer required for achieving the desired pH value.

The invention will now be further explained by means of the following non-limiting example.

EXAMPLE

This example, which refers to FIG. 2, illustrates how D-luciferin analogs (in this case L-luciferin) and pyrophosphate could be used together so that a reagent with a stable light level is achieved already at a reasonable degree of inhibition. The luciferase used in the example has been purified by means of isoelectric focusing. In FIG. 2 the light intensity is shown as a function of time after adding a final concentration of $10^{-6}$ M ATP to the reaction mixture. In the reaction mixture (final volume 1 ml) there is comprised in all cases luciferase, D-luciferin (100 $\mu$g/ml), magnesiumacetate (10mM), bovine serum albumin (0.1%), EDTA (2mM), and 0.1 M tris (hydroxymethyl) aminometanbuffer adjusted to pH 7.75 by using acetic acid.

FIG. 2a shows the light curve obtained without any further additives. A reagent with a declining level according to FIG. 2a is not applicable for continous measurement of ATP-converting systems. FIG. 2b shows the effect of the addition of L-luciferin (10 $\mu$g/ml) resulting in an inhibition of about 70%. The decline of the curve is acceptable but the initial peak makes the reagents not applicable at high ATP concentrations for continuous measurements in ATP converting systems. When using higher concentrations of the additive and thus a higher degree of inhibition one will however obtain straight light curves and applicable reagents. In FIG. 2c there is shown the effect of pyrophosphate ($10^{-6}$ M). The decline of the light curve is still too big and there is a small initial peak. At higher and more inhibiting concentrations of the additive the light curve will be more straight. FIG. 2d shows the effect of L-luciferin (10 $\mu$g/ml) and pyrophosphate ($10^{-6}$ M). The decline as well as the initial peak has in this case been almost completely eliminated. This reagent is then well suitable for analytical purposes. Only the reagents which contain L-luciferin (2b and 2d) apparently saturated with respect to luciferin (D+L, see above) and only these reagents will consequently give the maximum analytical accuracy.

We claim:

1. A process for the determination of ATP concentrations by contacting the sample to be assayed, with a bioluminescence reagent based on D-luciferin, luciferase and metal ions, a reaction being obtained wherein ATP and D-luciferin are bound to the luciferase and light is emitted, and by measuring the intensity of the emitted light, which intensity is a measure of the ATP concentration, characterized by using in the determination at least one competitive inhibitor of the reaction in the form of a D-luciferin analogue.

2. A process according to claim 1, characterized by using the D-luciferin analogue at a concentration which gives an inhibition of at least 25%, preferably 50–90%, of the light intensity.

3. A process according to claim 1 or 2, characterized by using L-luciferin as the D-luciferin analogue.

4. A process according to claim 1, characterized in that also pyrophosphate is used in the determination.

5. A process according to claim 4, characterized by using the pyrophosphate at a highest concentration of $10^{-4}$ M, preferably at most $10^{-5}$ M.

6. A process according to claim 1, characterized in that also coenzyme A is used in the determination.

7. A process according to claim 1, characterized by using a reagent containing luciferase that has been purified by isoelectric focusation.

8. A process according to claim 1, characterized by using a reagent containing luciferase with an additive of bovine serum albumine, thiol compounds and/or EDTA.

9. A bioluminescence reagent for use in the determination of ATP-concentrations, which reagent is based on D-luciferin, luciferase and metal ions, characterized in that it also contains at least one competitive inhibitor in the form of a D-luciferin analogue.

10. A reagent according to claim 9, characterized in that the D-luciferin analogue is present at a concentration which gives an inhibition of at least 25%, preferably 50–90%, of the light intensity.

11. A reagent according to claim 9 or 10, characterized in that the D-luciferin analogue is L-luciferin.

12. A reagent according to claim 9, characterized in that it also contains pyrophosphate.

13. A reagent according to claim 12, characterized in that the pyrophosphate is present at a highest concentration of $10^{-4}$ M, preferably at most $10^{-5}$ M.

14. A reagent according to claim 9, characterized in that it also contains coenzyme A.

15. A reagent according to claim 9, characterized in that it contains luciferase that has been purified by isoelectric focusation.

16. A reagent according to claim 9, characterized in that it contains luciferase with an additive of bovine serum albumine, thiol compounds and/or EDTA.

* * * * *

UNITED STATES PATENT OFFICE
CERTIFICATE OF CORRECTION

Patent No. 4,246,340　　　　　　　　　Dated January 20, 1981

Inventor(s) Lundin et al.

It is certified that error appears in the above-identified patent and that said Letters Patent are hereby corrected as shown below:

[30]　　　　　Foreign Application Priority Data

May 31, 1978 [SE]　Sweden ............. 7806296

Signed and Sealed this

First Day of September 1981

[SEAL]

Attest:

GERALD J. MOSSINGHOFF

Attesting Officer　　　Commissioner of Patents and Trademarks